United States Patent [19]

Nishino et al.

[11] 4,410,597

[45] Oct. 18, 1983

[54] POLYURETHANE RESINS AND POLYURETHANE RESIN COATING COMPOSITIONS

[75] Inventors: Masaki Nishino, Kawasaki; Yutaka Yasuhara, Nagoya; Tadanori Fukuda, Otsu; Sadayuki Sakamoto, Koga, all of Japan

[73] Assignee: Toray Industries, Inc., Tokyo, Japan

[21] Appl. No.: 108,865

[22] Filed: Dec. 31, 1979

[30] Foreign Application Priority Data

Dec. 28, 1978 [JP] Japan ................................. 53-161804

[51] Int. Cl.$^3$ ........................ B32B 27/40; C08G 18/34
[52] U.S. Cl. .............................. 428/423.1; 427/385.5; 427/388.2; 427/409; 428/425.8; 528/75; 528/80; 528/83; 528/85
[58] Field of Search ................... 528/44, 83, 85.75, 80; 521/99; 321/155, 160; 260/453 PH, 453 AL, 583 P; 428/423.1, 425.8; 427/388.2, 409, 385.5

[56] References Cited

U.S. PATENT DOCUMENTS

| | | | |
|---|---|---|---|
| 2,642,449 | 6/1953 | Morningstar et al. | 260/453 PH |
| 2,865,940 | 12/1958 | Nobis et al. | 260/453 PH |
| 3,455,883 | 7/1969 | Kamal et al. | 260/453 PH X |
| 3,960,916 | 6/1976 | Fuchs et al. | 260/453 PH |
| 4,007,151 | 2/1977 | Ogawa et al. | 528/44 X |
| 4,045,462 | 8/1977 | Bock et al. | 260/453 |

FOREIGN PATENT DOCUMENTS 44-28287 11/1969 Japan.

OTHER PUBLICATIONS

Chemical Abstracts vols. 41-90 "Formulas $C_{13}$–$C_{19}$", (1947-1979).
Chemical Abstracts vol. 72, 1970 Article 42,743m "1,6,11-Triaminoundecane".

Primary Examiner—Thurman K. Page
Attorney, Agent, or Firm—Austin R. Miller

[57] ABSTRACT

Polyurethane resins and polyurethane coating compositions are provided which exhibit enhanced resistance to weather. The resins comprise the reaction product obtained from reacting a polyol with 1,6,11-undecanetriisocyanate. The resin composition herein disclosed is readily adapted for use in either a one component-heat curing system or in a two component-polyol hardening system. In the one component system, the isocyanate group of the isocyanate compound is blocked by a blocking agent so as to ensure stability of the coating at room temperature. After application, the coating resin is heated to effect reaction of a hydroxyl group from the polyol with an isocyanate group to cause hardening of the film. In the two component system, the polyol-pigment liquid, liquid "A", is mixed with the trifunctional isocyanurate compound (above noted) and solvent, liquid "B".

13 Claims, No Drawings

POLYURETHANE RESINS AND POLYURETHANE RESIN COATING COMPOSITIONS

BACKGROUND OF THE INVENTION

1. Field of the Invention

The present invention relates to polyurethane resins which are useful in producing polyurethane resin coatings which, in particular, exhibit excellent weather resistance.

2. Description of the Prior Art

Polyurethane resins are classified into two types by the kind of isocyanate compounds contained in them. The classification thus includes "yellowing" and "non-yellowing" types. Isocyanates which have hitherto been in use as ones giving polyurethane resins of the non-yellowing type include: such aliphatic isocyanates as hexamethylenediisocyanate, isophoronediisocyanate, 2,2,4-trimethylhexamethylenediisocyanate, dicyclohexylmethanediisocyanate, etc.; and xylylenediisocyante, etc. Whilst non-yellowing type polyurethane resins obtained by causing these isocyanates to react with polyols have been employed as coating materials, there still remained many problems to be solved in using them for such purpose.

One of these problems is their toxicity. Since isocyanate compounds are substances which are chemically highly reactive, they are very dangerous when used by persons who are of an allergic constitution or have weak respiratory organs. Because of this, the limit of concentration in the atmosphere of, for instance, monomers of toluenediisocyanate, diphenylmethanediisocyanate, etc., was fixed at 0.02 ppm by the Commission of the American Conference of Governmental Industrial Hygienists. For such reason, the unmodified isocyanate monomers are seldom used in polyurethane coatings. However, in special cases, they are used after having been modified into prepolymers—adducts obtained by adding them to trimethylolpropane, ethylene glycol, etc. This modification has the effect of lowering vapor pressure, thereby reducing the toxicity and bad odor of the isocyanate. In addition, modification allows adjustment of the reactivity of the isocyanate and diversification in the type of coatings to be realized.

Since, however, it is difficult to wholly eliminate isocyanate monomers in the prepolymer additions during commercial operation, the fact is, that one still smells a strong irritating odor while he is engaged in the work of preparing coating materials or of applying coats. Many people complain of the symptoms of respiratory diseases which are peculiarly contracted by inhaling isocyanate vapors. With an increase in the use of polyurethane products, this question has now more than ever been brought much to the fore.

With the isocyanate additions and while these materials are in storage, in particular, it is said that there occurs dissociation of diisocyanates into highly toxic monomers, depending upon the storage conditions, and this constitutes an uneasy factor for those concerned including chemical engineers and operators alike. Under such circumstances, certain measures are being taken for improvement of the working environment. For instance, provision of good ventilation, is necessary so that the operators will not directly inhale the isocyanate compound vapors. However, the state of things in this connection is still far from being satisfactory.

The second question in the conventional technology is that there remains, with the conventional coatings, much to be desired with respect to their weather resistance. Although the non-yellowing type polyurethane resins were originally developed with a view to improving the weather resistance of coatings, they are not, as yet, sufficiently resistant to weather when used as coatings for items which are exposed to severe outdoor conditions over a long period of time, such as automobiles, railroad carriages, aircrafts, vessels, building materials, and so forth.

The third question concerning polyurethane coating materials, according to conventional techniques, is that the range in which the selection of solvent composition can be made is not necessarily wide enough, and that, if the amount of solvent is reduced from the viewpoint of energy saving and prevention of environmental pollution, the coating efficiency of the resultant product, being the so-called "high solid type" coating with a high concentration of polyurethane resin, is impaired because of its high viscosity.

SUMMARY OF THE INVENTION

The main object of the present invention is to provide polyurethane resins and polyurethane resin coatings having a high resistance to weather.

Another object of this invention is to provide polyurethane resin coating compounds which afford an improved coating work efficiency.

Still other objects of the present invention will become clear from the description to follow.

We have found that a novel aliphatic triisocyanate, 1,6,11-undecane triisocyanate, can be utilized for preparing a polyurethane resin film coat having an excellent weather resistance, and that the objects of the present invention can be therefore attained.

The film coat of the present invention has, for its main ingredient, a polyurethane resin which is a reaction product obtained by causing a polyol to react with 1,6,11-undecane triisocyanate.

DETAILED DESCRIPTION OF THE PREFERRED EMBODIMENTS 1,6,11-Undecane triisocyanate, used for preparing the polyurethane resin of the present invention, belongs to a new type of aliphatic triisocyantes and possesses advantages over aliphatic polyisocyanates of the prior arts.

1,6,11-Undecane triisocyanate can be prepared from 1,6,11-undecane triamine by a conventional phosgenation method. The novel triisocyanate boils at 166° C. to 167° C. under a vacuum of 0.2 torr. This boiling point range will be appreciated to be well-balanced from the view-point of purification and toxicity. This isocyanate generates scarcely any odor or vapor irritating the nose, eyes, throat, etc., because of its low vapor pressure, whereas it can be easily purified by vacuum distillation.

This triisocyanate differs significantly from the other aliphatic isocyanates, such as hexemethylene diisocyanate or 2'-isocyanatoethyl-6-isocyanatocaproate by its substantially reduced toxicity and strong resistance to the action of alkaline substances. Some of these properties may be attributed to the chemical structure of the novel triisocyanate as it has neither any hetero-atoms such as oxygen and nitrogen, nor any unsaturated bonds in the molecule except for three NCO groups.

Moreover, the NCO group content in the novel triisocyanate reaches as high as about 45 weight percent, based on the total weight of the triisocyanate. Furthermore, the novel triisocyanate has low viscosity so that it does not necessarily require dilution with solvents for the purpose of lowering viscosity for practical usage.

Thus the novel triisocyanate is extremely suitable for preparing a non-yellowing type polyurethane resin.

A polyol as referred to in the present invention means a compound or polymer containing two or more hydroxyl groups per molecule.

As examples of polyols, there are diols, triols, tetraols, pentols and hexitols; while there are also such polymer polyols as polyester containing two or more hydroxy radicals per molecule (hereinafter called "polyester polyol"), polyether containing two or more hydroxyl groups per molecule (hereinafter called "polyether polyol"), acrylic polymer containing two or more hydroxyl radicals per molecule (hereinafter called "polyacryl polyol"), etc. In the present invention, there may be used either singly or as a mixture of two or more kinds. Hereunder are given further examples, in more particulars, of polyols.

Diols: ethylene glycol, propylene glycol, $\beta,\beta'$-dihydroxydiethyl ether (diethylene glycol), dipropylene glycol, 1,4-butylene glycol, 1,3-butylene glycol, polyethylene glycol, polypropylene glycol, polypropylene-polyethylene glycol, polybutylene glycol;

Triols: glycerine, trimethylol propane, 1,2,6-hexanetriol;

Tetraols: penta erythritol, 2-methylglucoside;

Hexitol: sorbitol;

Polyester polyols; These are polymerized by the condensation reaction between a polybasic acid, such as adipic acid, dimer acid, phthalic anhydride, isophthalic acid, etc., and a diol or triol, such as ethylene glycol, diethylene glycol, propylene glycol, trimethylol propane, glycerine, etc.

Polyether polyols: These are prepared by adding propylene oxide, ethylene oxide, or the like, to a polyhydric alcohol, such as glycerine, propylene glycol, etc. In this category are also included polyether polyols rich in hydroxyl radicals obtained by causing a multifunctional compound such as ethylenediamine, ethanolamine, etc. to react with ethylene oxide or propylene oxide.

Polyacryl polyols: Copolymers of an acrylic acid ester or methacrylic acid ester containing a hydroxyl group (as expressed by the following general formula) in combination with a monomer which is capable of being copolymerized with such:

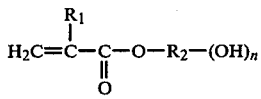

wherein
n = 1, 2 or 3
$R_1$ = hydrogen or methyl
$R_2$ = a remnant radical of substituent or nonsubstituent hydrocarbon with a carbon number of 2 to 12

Hereunder are enumerated examples of acrylic acid esters or methacrylic acid esters containing the aforesaid hydroxyl group. 2-hydroxyethyl acrylate, 2-hydroxypropyl acrylate, 2-hydroxybutyl acrylate, 2-hydroxyethyl methacrylate, 2-hydroxypropyl methacrylate, 3-hydroxypropyl methacrylate, 4-hydroxybutyl methacrylate, 2-hydroxypentyl methacrylate, methacrylic acid monoester of glycerine, acrylic acid or methacrylic acid monoester of trimethylol propane, 2-hydroxy-3-chloropropyl acrylate, 2-hydroxy-3-chloropropyl methacrylate, etc.

Out of these, the most desirable are: 2-hydroxyethyl methacrylate, 2-hydroxyethyl acrylate and 2-hydroxypropyl methacrylate.

Examples of monomers which are capable of being copolymerized with the above-mentioned acrylic acid or methacrylic esters containing a hydroxyl group are given below:

(1) acrylic acid or its esters, for example, acrylates of methyl, ethyl, propyl, butyl or 2-ethylhexyl (2) methyacrylic acid or its esters, for example, methacrylates of methyl, ethyl, butyl, decyl, 2-ethylhexyl or lauryl (3) styrene or its derivatives, for example, $\alpha$-methylstyrene, $\beta$-chlorostyrene, etc.

(4) vinyl esters, for example, vinyl acetate, vinyl propionate, vinyl isopropionate, etc.

(5) nitriles, for example, acrylonitrile, methacrylonitrile, etc.

Out of these, the most desirable are: methyl acrylate, ethyl acrylate, butyl acrylate, methyl methacrylate, butyl methacrylate, lauryl methacrylate, acrylic acid, methacrylic acid, styrene, acrylamide, vinyl acetate, etc.

To prepare polyacryl polyols best suited for purpose of this invention, it is desirable that the amount of each monomer used be selected from the following ranges:

(A) Hydroxylalkyl(meth)acrylate . . . 5 to 30 pct. by wt.

(B) Alkyl ester of acrylic acid and/or of methacrylic acid . . . 50 to 95 pct. by wt.

(C) Other monomer(s), as occasion demands . . . 0 to 50 pct. by wt.

(D) Acrylic acid or methacrylic acid . . . 0 to 10 pct. by wt.

If, of the foregoing, the amount of hydroxylalkyl(meth)acrylate is less than 5 pct. by wt., the degree of bridging by reaction with isocyanate compounds becomes too small and hence it will be impossible to obtain a film coat of such performance as was to be expected.

While the manufacture of polyacryl polyols by copolymerization of monomers, as described above, may be carried out by any one of such well known polymerization methods as solution, block, emulsion and suspension polymerization, the first mentioned method, i.e., solution polymerization, is generally employed.

Selection of the polyols may be made at one's discretion so as to fit a specific purpose, but, in general, the use of polyester polyols or polyacryl polyols is preferable.

As for the molecular weight of the polyols used, too, selection may be made from quite a wide range according to the specific purpose. For the "high solid type" coating, however, a range of 500 to 5,000, especially, 500 to 3,000, is preferred. More particularly, when polyester polyols are used, those with a molecular weight in the range of 500 to 1,000 are best suited for the purpose; while when polyacryl polyols are used, those with a molecular weight in the range of 1,000 to 3,000 may be utilized to best advantage. When manufacturing coatings which are not of the "high solid type", polyols with a molecular weight higher than ordinary are employed.

By making the proper choice of polyols to be used and by adjusting the NCO/OH mole percentage, the physical properties and hence efficiency of the product, such as the strength of film coat, flexibility, chemical resistance, solvent resistance, etc., can be modified in a wide range, thereby to make it suitable for specific purposes.

Compounds of which the NCO/OH mole percentage is in the range of 0.5 to 2.0 are suited for the manufacture of films and for the application of film coat. For polyurethane coatings, in particular, the range of 0.5 to 1.2 is preferred.

If the NCO/OH mole percentage is below the lowest figure, as above noted, the hot water and acid resistance of the resulting film coat is lowered, resulting in a poorer weather resistance. When it is above the highest figure, there also takes place a lowering of weather resistance.

Those compounds with an NCO/OH mole percentage in the range of 0.5 to 1.0 may be advantageously used for such fields as electrical insulation, capsulation, and manufacture of cast products.

When the NCO/OH mole percentage is in the range of 0.1 to 0.7, such compounds may be advantageously utilized for the manufacture of highly efficient adhesives or hardening agents. When, on the other hand, the NCO/OH mole percentage is greater, such compounds are suited for the manufacture of foam products. The foaming may be achieved by introducing a certain fixed amount of water or a blowing agent into the reaction products, by utilization of known foaming techniques.

The polyurethane resin coating of the present invention is adaptable to both the one-component and two-component types, but is more advantageous to use it as a two-component type coating.

(1) TWO-COMPONENT, POLYOL HARDENING TYPE

This is a two-component type polyurethane resin coating comprising a kneaded mixture of a polyol and a pigment, the latter being added at need ("A" liquid), and a trifunctional isocyanate of the present invention, diluted with a solvent as needed ("B" liquid). In use, the "A" and "B" liquids are mixed together and, when necessary, the viscosity is adjusted by the use of a thinner. For mixing the two liquids, a two-liquid gun may preferably be employed. It is desirable that the mixing ratio be determined in such a manner that the NCO/OH mole percent will be 0.5 to 2.0, the concentration of carbamide radical $5 \times 10^{-4}$ to $50 \times 10^{-4}$ moles per gram of the reaction product, and the bridging parameter 150 to 1,500.

The solvent in the "B" liquid, and the thinner for the mixture, which is used if needed, may be either the same or different; but, in the latter case, it is necessary that the two are compatible with each other. Further, these must not be ones which are reactive with isocyanates and polyols, such as ones containing active hydrogen atoms. Some examples of solvents that may be used are given below.

Hydrocarbon solvents: benzene, toluene, xylene, and aromatic naphtha.

Ester solvents: ethyl acetate, butyl acetate, cellosolve, hexyl acetate, amyl acetate, ethyl propionate, and butyl propionate Ketone solvents: acetone, methyl ethyl ketone, methyl isopropyl ketone, methyl isobutyl ketone, diethyl ketone, and cyclohexanone.

Glycol ester solvents: ethylene glycol monoethyl ether acetate, and diethylene glycol monoethyl ether acetate.

One of the characteristics of the present invention resides in the fact that, of the whole solvent composition, more than 50 pct. by wt. can be the aforesaid hydrocarbon solvent.

Further, the amount of solvent in the aforesaid "B" liquid can be as small as 0 to 50 pct. by wt., and this also constitutes a characteristic of the coating in accordance with the present invention. This makes it easier to obtain a "high solid type" coating—a contributing factor in improving the outward appearance of film coats.

As for polyols to be used, those which were previously mentioned, that is, polyester polyols, polyether polyols, polyacryl polyols, etc., are recommended. These are certain to give good results.

By combining the proper kinds of polyols and isocyanate compounds, it is possible to obtain coats of varied properties, from soft to hard and tough, all of which possess excellent resistance to weather, water, chemicals and staining. Coatings of this type are ordinarily used at temperatures ranging from room temperature to 120° C. They display an excellent adhesive property when used for the coating of such materials as ferrous and nonferrous metals, plastics, rubber, leather concrete, etc., and hence have a wide range of applications in such fields of industry as the manufacture of building materials, automobiles, machines and instruments, woodworks, aircraft, railroad carriages and ships; and so forth.

(2) ONE-COMPONENT, HEAT CURING TYPE

With coatings of the two-component, polyol hardening type which has been described above, the reaction progresses even at room temperature; hence there frequently arise cases where the pot life of coatings in use presents a problem.

In this type of coating, (one-liquid, heat curing type), the isocyanate group of the isocyanate compound is once blocked by the addition of a blocking agent so that the coating will be stable at room temperature. The coating, after having been applied, is heated to dissociate the blocking agent. The isocyanate group is thus activated again and is caused to react with the hydroxyl group to form a film coat. This method is best suited for such applications as the coating of automobiles on a manufacturing line, or the like, where it is necessary to ensure stability of the coating materials while they are in storage at room temperature.

As polyols to be combined with the blocked type isocyanate prepolymer, polyester polyols and polyacryl polyols may be used to best advantage.

As blocking agents for the purpose of masking the free isocyanate radical of the trifunctional isocyanate compounds used in the present invention, those which are in general use may be brought into employment. Hereunder are given some examples of such blocking agents: Phenol, m-nitrophenol, p-chlorophenol, catechol, ethyl malonate, acetylacetone, ethyl acetoacetate, cresol, ε-caprolactam, methyl ethyl ketoxime, cyclohexanoneoxime, butyl mercaptan, methanol, ethanol, ethylene chlorohydrin, etc.

Although the temperature at which the above-mentioned blocking agents are dissociated varies with the type of blocking agent used, it is generally accepted that heating to at least 120° C. is required. Since this type coating requires baking at a relatively high temperature, it has hitherto been in use mainly in such fields as the manufacture of electric wires, etc. It is expected, however, that there will be new developments in its utilization, such as adaptation to a powder paint with polyurethane resin base, to an aqueous emulsion paint, and so forth.

Solvents for this type of coating, which are used as occasion demands, are identical with those in the case of the two-component type coatings. In this instance, too, more than 50 pct. by wt. of the whole solvent composition can be hydrocarbon solvents.

The coating compounds according to the present invention can be applied to the desired articles by ordinary coating methods such as spray, brush or roller coating, or dipping. The compounds also permit the use of commonly used pigments and plasticizers, or other kinds of additives which are used in small amounts when preparing the paint or when applying it, provided that the amounts used are within the limit of the common practice. For the choice of pigments, it is necessary to pay attention to their water content, as well as to other properties similar to those noted above in conjunction with the selection of suitable solvent. It is to be noted that extenders, in particular, have a great water adsorbability.

Catalysts may also be used to accelerate drying and hardening. For instance, such tertiary amines as dimethylethanolamine, triethylenediamine, etc., and organic salts of tin such as stannous, dibutyl tin dilaurate, etc., may be employed.

The characteristics of the coating according to this invention are as follows:

(1) It excels in gloss retention and anti-cracking properties.

(2) It has an excellent resistance to acid and water. It is thought that, this comes from the fact that it hardens very quickly after application, and that such property is closely related to the network-like structure of the hardened coat produced by the trifunctional isocyanate compound used in the present invention.

(3) It facilitates an improvement in the outward appearance of the coat.

Whilst the luster and build of a coat are related to various factors, the influence of the coating on the under coat is a factor which must not be left unheeded. With the compounds of this invention, it is possible to use a variety of solvents and, in particular, aromatic compound solvents may be used. This permits a reduction in the influence of the coating on the under coat, for instance, primer surface. That is, the permeation of the solvent is kept to the minimum, helping to achieve an improvement in the outward appearance of the coat. Thus, it is best suited for such purposes as coating of automobiles, etc., where an emphasis is placed on a good outward appearance.

(4) It contributes to development of coatings of the "high solid type".

Amidst the recent moves for restriction on environmental pollution, the development of polyurethane resin coatings of the "high solid type" or of the solventless type is attracting much attention in concerned circles. Isocyanate as an ingredient of such coatings is required to have, like the polyol ingredient, a low viscosity at room temperature. As the trifunctional isocyanate used in the present invention has a low molecular weight, it has a low viscosity, and hence may be intended for the manufacture of coatings in a manner that will help prevent environmental pollution. It is also possible, by proper choice of the polyols to be used, to manufacture solventless coatings and thus to contribute to savings in resources or energy. The coating of the present invention is, because of its low viscosity, excellent in respect of coating work efficiency, too.

(5) Hardening speed is excellent.

Although the hardening speed at room temperature is not so clearly different from that of the coating materials on the market, it becomes considerably greater than the latter upon a rise in baking temperature. Thus, it is possible to shorten the time required for curing.

(6) Low toxicity.

Hexamethylenediisocyanate prepolymers or adducts have, in general, a pretty strong and irritating odor. This is because, it is said, of the existence of a very small amount of hexamethylenediisocyanate monomer in the prepolymers or adducts. With, on the other hand, the trifunctional isocyanate compounds employed in the present invention, the vapor pressure is remarkably low, and there is no liberation of volatile, high toxicity, ingredients while they are kept in storage. Also, their NCO content is higher than that of the coating materials on the market. Therefore, the coating of this invention emits little irritating odor which is peculiar to the isocyanate content of coatings. As the proportion of the isocyanate ingredient to that of the polyol ingredient may, in view of its high NCO content, be reduced, it is quite advantageous from the viewpoint of hygiene.

The polyurethane resin of the present invention may be put to a wide range of uses in various fields of industries besides its use as a coating material as above noted.

For instance, those compounds with an NCO/OH mole percentage in the range of 0.5 to 1.0 may be used to advantage in such fields as electrical insulation and capsulation, and in the manufacture of cast products.

When the NCO/OH mole percentage is in the range of 0.1 to 0.7, such compounds may be advantageously utilized in the manufacture of highly efficient adhesives or hardening agents. When, on the other hand, the NCO/OH mole percentge is greater, such compounds are suited for the manufacture of foam products. The foaming may be achieved by introducing a certain fixed amount of water or a blowing agent into the reaction products, by utilization of well known foaming techniques.

The present invention will now be further illustrated in the following examples. However, it is to be noted that these examples are given merely to explain and not to limit the invention, and that numerous changes may be made in the examples without departing from the spirit and scope of the invention as defined in the appended claims.

Several examples of embodiments of the present invention are now recited and compared with a few comparative examples. The phrase "Part or parts", of the composition shown in the examples, means "part or parts by weight" unless noted otherwise.

PREPARATION OF 1,6,11-UNDECANETRIISOCYANATE

To a solution of 100 g of 1,6,11-undecanetriamine in 100 ml of methanol, 136 ml of concentrated (35 wt. percent) hydrochloric acid was added dropwise while cooling to maintain the reaction temperature at below 30° C. The reaction mixture was concentrated by means of a rotary evaporator in vacuo on a hot water bath to yield a thick oil. The oil, which on digestion with 500 ml of i-propyl alcohol was similarly concentrated, was evacuated at about 80° C. under a vacuum below 5 torr for 10 hrs. to give white solids of 1,6,11-undecanetriamine trihydrochloride. The solids thus obtained were crushed and pulverized in a mortar with a pestle under a dry atmosphere to result in a fine powder, having particle sizes of below 175 μm diameter and capable of passing through a screen of 80 mesh.

A four-necked, round-bottomed flask fitted with a mechanical stirrer, a thermometer, a gas inlet almost reaching the bottom of the flask, and a condenser, was charged with 66.5 g of this triamine hydrochloride powder and 665 ml of o-dichlorobenzene. The mixture was phosgenated by using a phosgene flow of approximately 30 g/hr. The reaction was started at 130° C. and gradually heated to 140° C. after 4 hours, then was maintained for 7 hours at 140° C. and further maintained for 4 hours at 150° C. As the reaction proceeds, the starting powder suspended in the mixture was dissolved. After cooling to room temperature and filtration, the solvent was distilled off at about 40° C. under reduced pressure of about 4 torr, and the product was distilled at 166° C. to 167° C. at 0.2 torr to give 47.2 g of 1,6,11-undecane triisocyanate:

$n_D^{20}$—1.4720

Analysis—Calc'd for $C_{14}H_{21}N_3O_3$ (percent): C 60.19; H 7.58; N 15.05, Found C 59.89; H 7.55; N 14.82.

High-resolution MS—Cal'd for $C_{14}H_{21}N_3O_3$, $M^+/e=279.1584$, Found $M^+/e=279.1585$.

IR Spectra $(cm^{-1})$—2940, 2869, 2260(NCO), 1460, 1360.

NMR Spectra (ppm)—1.45(singlet, 16H), 3.4(distorted triplet, 5H)

EXAMPLE 1

A vessel equipped with a mechanical stirrer, a thermometer, a reflux condenser and a nitrogen gas inlet tube, was charged with the following solvents under a nitrogen atmosphere, and heated to 90°–95° C.

| Xylole | 50 parts |
|---|---|
| Butylacetate | 50 parts |

The following mixture was dripped in a constant rate over a period of 3 hours.

| Styrene | 34.0 parts |
|---|---|
| n-Butylacrylate | 38.0 parts |
| β-Hydroxyl methacrylate | 23.4 parts |
| Acrylic acid | 0.4 parts |
| Azobisisobutyronitrile | 1.2 parts |

After completion of dripping of the mixture, the mixture was maintained at 90°–95° C. for one hour, and then 0.7 parts of azobisisobutyronitrile were added 4 times at intervals of 30 minutes, and after that, the mixture was further held for one hour.

The resulting solution of acrylic polyol was a clear liquid and its Garnder Viscosity was T-U at 25° C. The total solids content was 50%. The OH Value of this solution was 50 and the calculated average OH value per one copolymer molecule was 12.9. The molecular weight ($\overline{Mn}$) of this copolymer was 14,500.

This white enamel was diluted with a thinner composed of toluol and cellosolveacetate (50/50 wt %) with a settlement time of 18 seconds using Ford Cup No. 4. This diluted composition was sprayed onto zinc phosphate treated steel panels coated with primer surfacer No. 114 (Kansai Paint Co. Ltd.) and polished with sand paper, to form a smooth film at a dry film thickness of about 40v. Panels thus coated were cured at room temperature (23° C.) for 7 days. The resulting films were tough and had excellent properties for acid resistance and warm water resistance as shown in Table 1. Also the exposure test results indicated no significant difference in yellowing resistance between the films of this example and coating film obtained by using commercially available aliphatic polyisocyanate, especially Desmodur N-75 (Bayer AG).

EXAMPLE 2

The apparatus of Example 1 was charged with the following solvents under an atmosphere of nitrogen, and heated to 80°–85° C.

| Xylole | 80 parts |
|---|---|
| Butylacetate | 20 parts |

The following mixture was dripped in at a constant rate over a period of 3 hours.

| Styrene | 25.0 parts |
|---|---|
| Methyl methacrylate | 25.0 parts |
| n-Butylmethacrylate | 21.0 parts |
| n-Butylacrylate | 14.0 parts |
| β-Hydroxylmethacrylate | 12.0 parts |
| Acrylic acid | 0.7 parts |
| Azobisisobutyronitrile | 1.2 parts |

After completion of dripping of the mixture, the mixture was maintained at 80°–85° C. for 2 hours, and then 0.5 parts of azobisisobutyronitrile were added 4 times at intervals of 2 hours. After that, the mixture was held for further for 3 hours. The resulting acrylic polyol solution was a clear liquid and its Gardner Viscosity was V–W at 25° C., the total solids content was 50%. The molecular weight ($\overline{Mn}$) of the copolymer was 11,700, and the OH value of the solution was 25. Accordingly the calculated average OH value per one copolymer molecule was 5.2.

Using the same method described in Example 1, 1,6,11-undecanetriisocyanate and a panel was coated therewith, followed by curing of the resin. The resulting film exhibited excellent performance in uniform high gloss, higher reactivity with polyol, acid resistance and warm water resistance as shown in Table 2. The yellowing resistance of the exposure test film was as good as the film obtained by using an available aliphatic polyisocyanate.

COMPARATIVE EXAMPLES 1-2

In these Examples, the paint and its curing film were prepared using "Desmodur N-75" (the biuret type based on hexamethylene diisocyanate, registered trademark of Bayer AG) instead of 1,6,11-undecanetriisocyanate as used in Examples 1 and 2. The properties of the films were compared in Tables 1 and 2.

White enamel was prepared by mixing following two polyol components with "Desmodur N-75" at an NCO-/OH ratio of 1.0. The polyol components were prepared by mixing each of the acrylic polyols obtained in Examples 1 and 2 with TiO$_2$ "R-930" (registered trademark of Ishihara Sangyo Kaisha, Ltd.) glass beads using a Paint Conditioner (shaker). The white enamel compositions thus obtained were diluted to a settlement time of 18 seconds using Ford Cup No. 4 and then the diluted compositions were coated onto steel panels by the same method as in Example 1.

The paints in accordance with the present invention were higher in non-volatility properties at spray operation (thus saving raw materials), and they exhibited good compatibility with the solvents. The cured films, in accordance with the invention, had approximately the same level of practical properties as the films obtained by using "Desmodur N-75", but exhibited excellent acid resistance in contrast to the "Desmodur N-75" films.

TABLE 1

| Test Items | Condition | Example 1 1,6,11-Undecane-triisocyanate | Comparative Example 1 "Desmodur N-75" | Example 2 1,6,11-Undecane-triisocyanate | Comparative Example 2 "Desmodur N-75" |
|---|---|---|---|---|---|
| Initial hardness rate | | ◯ | ◯ | ◯ | ◯ |
| Gloss | 60° | 95 | 92 | 93 | 93 |
| Pencil hardness | | F | F | F | F |
| Impact resistance ½", 1000 g | Du Pont | 30 cm | 30 cm | 25 cm | 20 cm |
| Erichsen | | 7.0 mm | 6.5 mm | 7.7 mm | 7.5 mm |
| Adhesion | Cross Cut | 100/100 | 100/100 | 100/100 | 100/100 |
| Warm water resistance | 50° C. × 24 hr | ◎ | Δ | ◎ | Δ |
| Acid resistance | 40 vol % $H_2SO_4$ 55° C. × 5 hr | ◎ | x | ◎ | x |
| Solvent resistance | Naphtha No. 5/ toluol = 6/4 dipping for 10 min | ◯ | ◯ | ◯ | ◯ |
| " | Xylole rubbing 30 times | ◯ | ◯ | Δ | Δ |
| Yellowing index (YI) | UV* 0 hr | 2.5 | 3.2 | 2.8 | 3.0 |
| " | UV* 200 hr | 10.0 | 12.1 | 9.6 | 11.2 |
| YI | 200 hr | 7.6 | 8.9 | 7.4 | 8.2 |
| E (Lab) | 200 hr | 5.0 | 5.5 | 5.5 | 5.0 |

Legend
*Sterilization Lamp GL 15 (15 W) made by Tokyo Shibaura Electric Co., Ltd.,
wave length: 254 mm,
radiation strength from distance 20 cm: 600 μW/cm²
Pigmentation: PWC 50%
Curing condition: 23° C. × 7 days
Evaluated level sign:
◎ excellent
◯ good
Δ fair
x poor

TABLE 2

| | Example 1 | Comparative Example 1 | Example 2 | Comparative Example 2 |
|---|---|---|---|---|
| polyol OH value | 50 | 50 | 25 | 25 |
| Isocyanate | 1,6,11-Undecane triiso-cyanate | "Desmodur N-75" | 1,6,11-Undecane triiso-cyanate | "Desmodur N-75" |
| Test items | | | | |
| Compatibility | | | | |
| toluol/cellosolve acetate 50:50 | ◯ | ◯ | ◯ | ◯ |
| toluol | ◯ | Δ (slightly opaque) | ◯ | Δ (slightly opaque) |
| Film appearance* | ◎ | ◯ | ◎ | ◯ |
| Spraying solids content Ford Cup No. 4 20 seconds | 55% | 49% | 54% | 48% |

*used a thinner comprising toluol and cellosolve acetate (50/50)
Pigmentation: PWC 50%
Curing condition: room temp (23° C.) × 7 days
Substrate: Zinc phosphate treated steel coated with primer surfacer No. 114 and polished with sand paper
Evaluated level sign: same as Table 1

EXAMPLE 3

Polyester polyol was prepared from the following mixture:

| | |
|---|---|
| Neopentyl glycol | 126.9 parts |
| Trimethylol propane | 22.1 parts |
| Adipic acid | 72.3 parts |
| isophthalic acid | 123.2 parts |

This mixture was charged into a vessel and heated to 200° C. for 30 minutes with stirring. Then until the Gardner viscosity raised to F, while the acid value decreased to about 10 and the OH value decreased to about 100 in a MEK solution (N.V.=60%), the mixture was maintained for about 15 minutes. After that, this mixture was cooled and diluted with MEK solvent to a non-volatility property of 60%, and thus the polyester polyol solution was obtained.

Then, this solution and 1,6,11-Undecanetriisocyanate were mixed uniformly at an NCO/OH ratio of 1.0. This composition was coated onto a substrate and cured. The resulting film had high gloss and excellent mechanical properties.

Although this invention has been described with reference to certain particular processing conditions, ompounds, and other parameters, it will be appreciated that many variations may be made without departing from the spirit and scope of the invention as defined in the appended claims.

What we claim is:

1. A polyurethane resin having an excellent weather resistance, which resin is a reaction product obtained by causing a polyol to react with 1,6,11-undecanetriisocyanate.

2. A polyurethane resin as claimed in claim 1, wherein the molecular weight of the polyol is in the range of 500 to 5,000.

3. A coated article which comprises a substrate and a film coating adhered thereon, said film coating comprising a polyurethane resin, the resin being a reaction product obtained by causing a polyol to react with 1,6,11-undecanetriisocyanate.

4. The article as claimed in claim 3, wherein the molecular weight of the polyol is in the range of about 500 to 5,000.

5. The article as claimed in claim 3, wherein the polyol is a polyester polyol, the molecular weight of the polyester polyol being in the range of about 500 to 1,000.

6. The article as claimed in claim 3, wherein the polyol is a polyacryl polyol, the molecular weight of the polyacryl polyol being in the range of about 1,000 to 3,000.

7. The article as claimed in claim 3, wherein the NCO/OH mole percentage is in the range of about 0.5 to 1.2.

8. The article as claimed in claim 6, wherein the polyacryl polyol is a copolymer composed mainly of hydroxyalkyl acrylate and/or hydroxyalkyl methacrylate, and an alkyl ester of acrylic acid and/or an alkyl ester of methacrylic acid.

9. A two-component type polyurethane resin coating composition composed of:
   (a) a kneaded mixture of a polyol and a pigment which is added to it as needed; and
   (b) 1,6,11-undecanetriisocyanate which has been diluted with a solvent as needed, the amount of solvent in (b) being about 0 to 50 pct. by wt.

10. A two-component type polyurethane resin coating composition comprising:
    (a) a kneaded mixture of a polyol and a pigment which is added as needed; and
    (B) 1,6,11-undecanetriisocyanate which has been diluted with a solvent as needed, the amount of solvent in (b) being greater than about 50% by weight based upon the combined weight of the solvent and 1,6,11-undecanetriisocyanate.

11. A one-component type polyurethane resin coating composition comprising a polyol, and 1,6,11-undecanetriisocyanate, the isocyanate group of the 1,6,11-undecanetriisocyanate being blocked with a blocking agent.

12. A coating composition as claimed in claim 11, further comprising a solvent which is added as needed to the 1,6,11-undecanetriisocyanate, wherein more than about 50 pct. by wt. of the solvent is provided in the solvent 1,6,11-undecanetriisocyanate mix, based upon the weight of the solvent and 1,6,11-undecanetriisocyanate.

13. A coating composition as claimed in claim 9 or 10, wherein a thinner is also added to (a) and (b).

* * * * *